US00PP16559P3

(12) United States Plant Patent

Nicolai

(10) Patent No.: US PP16,559 P3
(45) Date of Patent: May 23, 2006

(54) APPLE TREE NAMED 'NICOGREEN'

(50) Latin Name: *Malus communis Mill.*
Varietal Denomination: Nicogreen

(75) Inventor: Johan Nicolai, Sint-Truiden (BE)

(73) Assignee: Better3Fruit N.V. (BE)

( * ) Notice: Subject to any disclaimer, the term of this patent is extended or adjusted under 35 U.S.C. 154(b) by 0 days.

(21) Appl. No.: 10/293,208

(22) Filed: Nov. 12, 2002

(65) Prior Publication Data

US 2003/0121085 P1 Jun. 26, 2003

Related U.S. Application Data

(60) Provisional application No. 60/338,027, filed on Nov. 13, 2001.

(51) Int. Cl.
*A01H 5/00* (2006.01)

(52) U.S. Cl. ..... Plt./172

(58) Field of Classification Search ..... Plt./72, Plt./161

See application file for complete search history.

(56) References Cited

PUBLICATIONS

UPOV–ROM GTITM Computer Database, 2003/01, GTI Jouve Retrieval Software, citation for 'Nicogreen'.*

Corresponding Australian PBR Application No. 2004/318 filed Dec. 2003, 2004.

Corresponding Swiss PBR Application No. 04–2178 filed Dec. 21, 2004.

* cited by examiner

*Primary Examiner*—Bruce R. Campell
*Assistant Examiner*—S. B. McCormick-Ewoldt

(74) *Attorney, Agent, or Firm*—Foley & Lardner LLP

(57) ABSTRACT

A new and distinct apple tree named 'Nicogreen'. The new variety is the result of a cross between 'Delcorf' and 'Granny Smith,' and is most similar in appearance to 'Granny Smith'. The new variety is distinguishable from 'Granny Smith' by its early maturation, which occurs approximately six weeks before 'Granny Smith.'

1 Drawing Sheet

Latin name of the genus and species of the plant claimed: *Malus communis Mill.*
Variety denomination: 'Nicogreen'.

STATEMENT REGARDING FEDERALLY SPONSORED RESEARCH OR DEVELOPMENT

None.

BACKGROUND OF THE INVENTION

The present invention relates to a new and distinct cultivar of apple tree, botanically known as *Malus communis Mill.* and hereinafter referred to by the name 'Nicogreen'. This new and distinct cultivar was bred by inventor, Johan Nicolai, in Sint-Truiden, Belgium.

'Nicogreen' originated as a controlled cross between 'Delcorf' (unpatented) and 'Granny Smith' (unpatented). It most closely resembles 'Granny Smith' in appearance, although fruit of 'Nicogreen' matures approximately 6 weeks before 'Granny Smith.' Other differences between 'Nicogreen' and its parents are shown in the table below:

| Characteristic | 'Nicogreen' | 'Granny Smith' | 'Delcorf' |
|---|---|---|---|
| Fruit Skin color | Green | Green (greener than 'Nicogreen') | Yellow |
| Overcolor of fruit | Yellow | No blush | Orange red, striped |
| Flesh Color | White | White | Cream |

The new variety has been asexually propagated by T-budding and bench grafting onto 'M9' and 'MM111' rootstocks, and has been demonstrated to remain true to type through successive generations.

BRIEF DESCRIPTION OF THE PHOTOGRAPH

The FIGURE illustrates the fruit of the new variety, 'Nicogreen.'

DETAILED DESCRIPTION OF THE VARIETY

The following is a detailed botanical description of the new and distinct variety of apple tree, based on observations of specimens grown in Sint-Truiden, Belgium. The observed plants were five years old. Colors are described according to The Royal Horticultural Society Colour Chart (R.H.S.), except where general colors of ordinary significance are used. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant, or any group of plants of the new variety may vary from the stated average.

All trees of 'Nicogreen', insofar as they have been observed, have been identical in all the characteristics described below.

Parentage: 'Delcorf' (unpatented) and 'Granny Smith' (unpatented).

Classification:

*Botanical.*—*Malus communis Mill.*

Propagation: Holds to distinguishing characteristics through succeeding asexual propagations by T-budding and bench grafting onto 'M9' and 'MM111' rootstocks.

*Locality where grown and observed.*—Sint-Truiden, Belgium.

Tree:

*Age.*—Observed plants were five years old.
*Vigor.*—Medium (compare to 'Golden Delicious').
*Trunk diameter.*—40 mm at 50 cm above union.
*Height.*—2.5 m.
*Number of lateral branches.*—9.
*Length of lateral branches.*—1.6 m total length (3 to 4 years old branches). Approximately 0.70 m (new 1 year old shoots).
*Crown diameter.*—1.2 m.
*Bark color.*—Brown-grey (N199B).
*Branch diameter.*—16 mm.
*Branch color.*—Brown-grey (N199C), darker and greyer than 'Granny Smith'.
*Lenticels.*—Round and elongated, 1–1.5 mm. Approximately 5 lenticels/cm$^2$.

Leaves:

*Leaf length.*—110 mm.
*Leaf width.*—65 mm.
*Leaf margin.*—Irregular, every 1–3 mm, pointed.
*Leaf color* (*based on mature leaf*).—Upper surface — green, shiny (137A). Lower surface — pale green (138B).
*Leaf texture.*—Slightly hairy.
*Leaf shape.*—Apex: Obtuse; Base: Rounded.
*Petiole length.*—32 mm.
*Petiole color* (*based on mature leaf*).—Green (142B).
*Vein color.*—Yellow-green (145D).
*Venation pattern.*—Pinnate.
*Stipules.*—Relatively wide, 3–4 mm wide, 15–18 mm long.

Flowers:

*Bud length.*—13 mm.
*Bud diameter.*—8 mm.
*Bud color.*—White-grey.
*Time of beginning of flowering* (*10% open flowers*).—Medium (compare to 'Cox's Orange Pippin').
*Petal length.*—26.25 mm+/−3.14 mm.
*Petal width.*—16.09 mm+/−1.73 mm.
*Petal color* (*determined on an open flower*).—Upper surface — white (155B). Lower surface — red-purple (N57D).
*Petal color* (*determined at balloon stage*).—Red-purple (59D).
*Petal margin.*—Smooth.
*Petal texture.*—Hairy.
*Flower diameter.*—53.92 mm+/−2.84 mm.

Fruit:

*Fruit average weight.*—240 g.
*Fruit shape.*—Oblong (compare to 'Gravenstein').
*Fruit size.*—Height: 78 mm; Width: 83 mm.
*Stem length.*—22 mm.
*Depth of stem basin.*—15 mm.
*Calyx.*—Depth: 10 mm; Width: 30 mm.
*Overcolor of skin.*—Yellow-Green (N151A) (compare to 'Granny Smith').
*Background color of skin.*—Yellow-Green (N144A) ('Golden' nr 2 C3(a)).
*Lenticels.*—White (N155A), +/−0.5 mm diameter, Approximately 5 lenticels/cm$^2$.
*Flesh color.*—White (155A).
*Seeds.*—Present.
*Seed color.*—Grey-orange (175A).
*Seed length.*—8.27 mm+/−0.51 mm.
*Seed number.*—5.47+/−3.07.
*Time of fruit ripening for eating.*—Medium (compare to 'Reine des Reinettes').
*Sensitivity to pests/disease.*—Not very sensitive.
*Sensitivity to scald.*—Not very sensitive.
*Winter hardiness.*—No problems observed during the winter climates of Northwest Europe and the Alps.
*Drought/heat tolerance.*—Good; a yellow blush appears in hot dry climates.
*Market use.*—Fresh market. Very firm juicy apple; better eating quality than 'Granny Smith'.
*Storageability.*—Very good (8.5 kgf/cm$^2$ penetrometer value after 9 months storage at 1° C., 1% $O_2$, 2.5% $CO_2$.

Reproductive organs:

*Stamen length.*—12.79 mm+/−0.93 mm.
*Stamen quantity.*—19.56+/−0.88.
*Stamen color.*—White (155C).
*Pollen color* (*color of mature pollen grains was determined*).—Yellow (5D).
*Pollination requirements.*—Golden Hornet, Golden Gem, Hilieri.
*Sepal length.*—8.65 mm+/−1.49 mm.
*Sepal width.*—4.14 mm+/−0.47 mm.
*Sepal quantity.*—5.
*Sepal color.*—Green (138B).
*Pistil length* (*total length determined by measuring length of the part where the pistils are attached together and the length of the part where they are separated*).—11.38 mm+/−0.79 mm.
*Pistil width* (*width was measured at the base of the pistil*).—0.85+/−0.12 mm.
*Pistil quantity.*—5.
*Pistil color.*—Yellow-green (145A).

I claim:

1. A new and distinct apple tree plant named 'Nicogreen', substantially as illustrated and described herein.

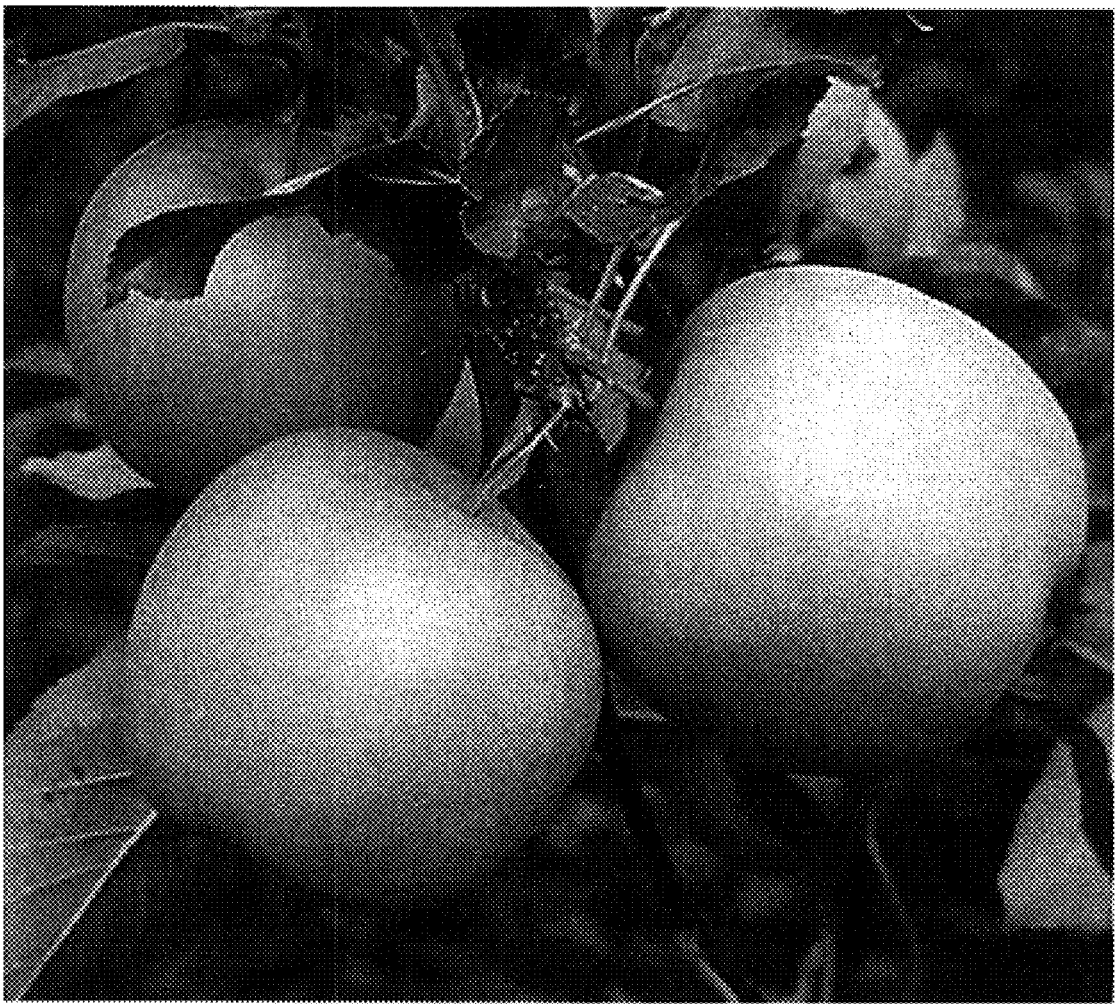

* * * * *